US00PP15733P2

(12) United States Plant Patent

Warren et al.

(10) Patent No.: US PP15,733 P2
(45) Date of Patent: Apr. 26, 2005

(54) *CALLA* LILY PLANT NAMED 'CRACKERJACK'

(50) Latin Name: ***Zantedeschia* sp.**
Varietal Denomination: Crackerjack

(75) Inventors: Andrew Geoffrey Fiennes Warren, Tauranga (NZ); Jacobus Petrus Spaans, Tauranga (NZ)

(73) Assignee: Bloomz Ltd., Tauranga (NZ)

( * ) Notice: Subject to any disclaimer, the term of this patent is extended or adjusted under 35 U.S.C. 154(b) by 71 days.

(21) Appl. No.: 10/766,113

(22) Filed: Jan. 27, 2004

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—Jondle & Associates P.C.

(57) ABSTRACT

A *calla* lily plant particularly distinguished by red spathe and maculated leaves.

3 Drawing Sheets

Genus and species: *Zantedeschia* sp.
Variety denomination: 'Crackerjack'.

BACKGROUND OF THE NEW PLANT

The present invention comprises a new and distinct cultivar of *calla* lily, botanically known as *Zantedeschia* sp., and hereinafter referred to by the cultivar name 'Crackerjack'. The new cultivar is asexually reproduced from vegetative cuttings and tissue culture resulting from the cross of the female parent 'Sunglow' (patent status unknown) and the male parent is an unnamed unpatented seedling from the Bloomz breeding pool.

'Crackerjack' is a product of a planned breeding program intended to create new *calla* lily plants with red spathes.

The new cultivar was created in 2000 in Tauranga New Zealand and has been asexually reproduced repeatedly by vegetative cuttings and tissue culture in New Zealand over a 3 year period. The present invention has been found to retain its distinctive characteristics through successive propagations; and this novelty is firmed fixed. 'Crackerjack' reproduces true to type through successive generations of asexual reproduction.

DESCRIPTION OF PHOTOGRAPH

This new *calla* lily plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
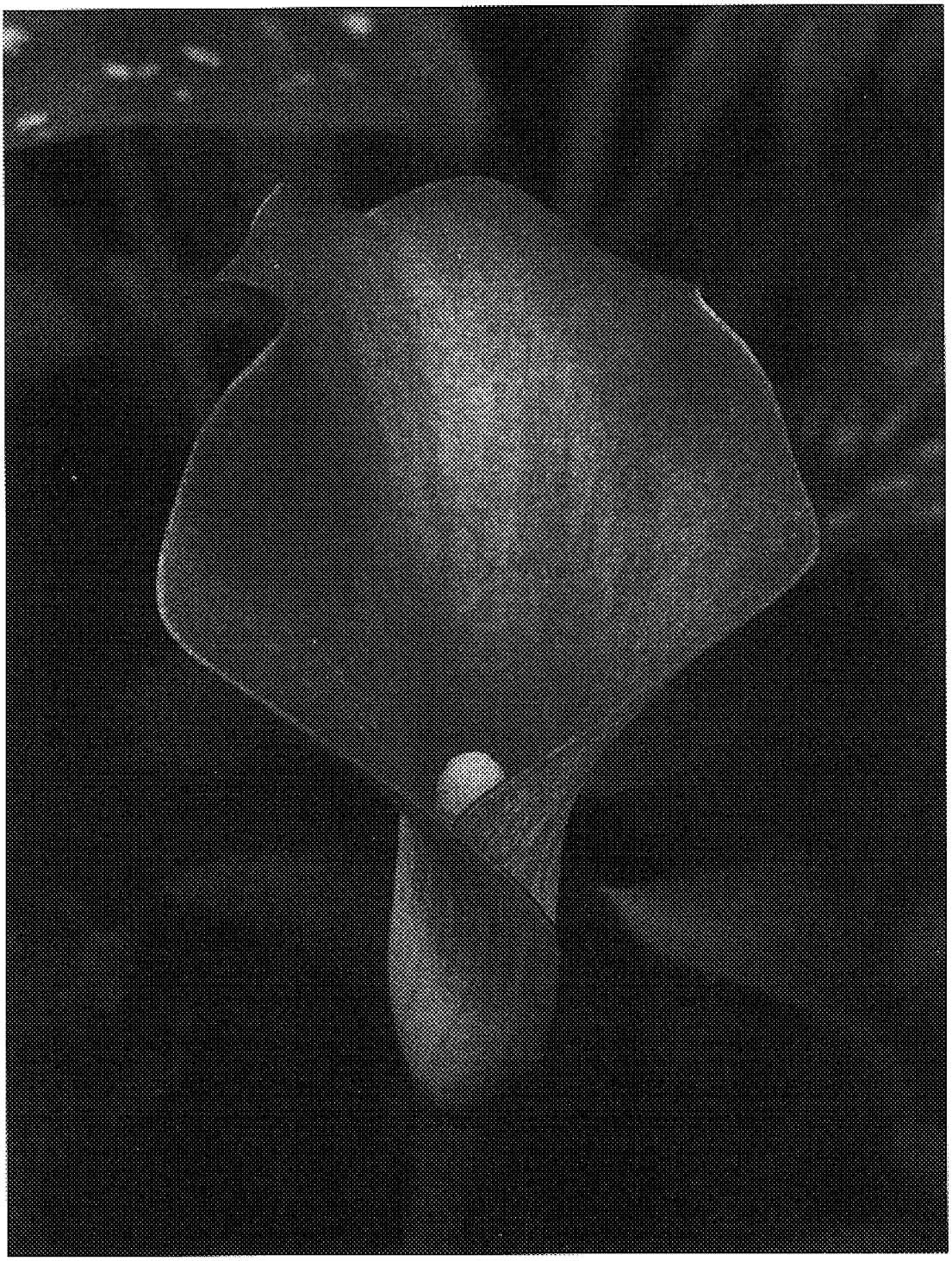
FIG. 1 shows the mature inflorescence.
Figure 2:
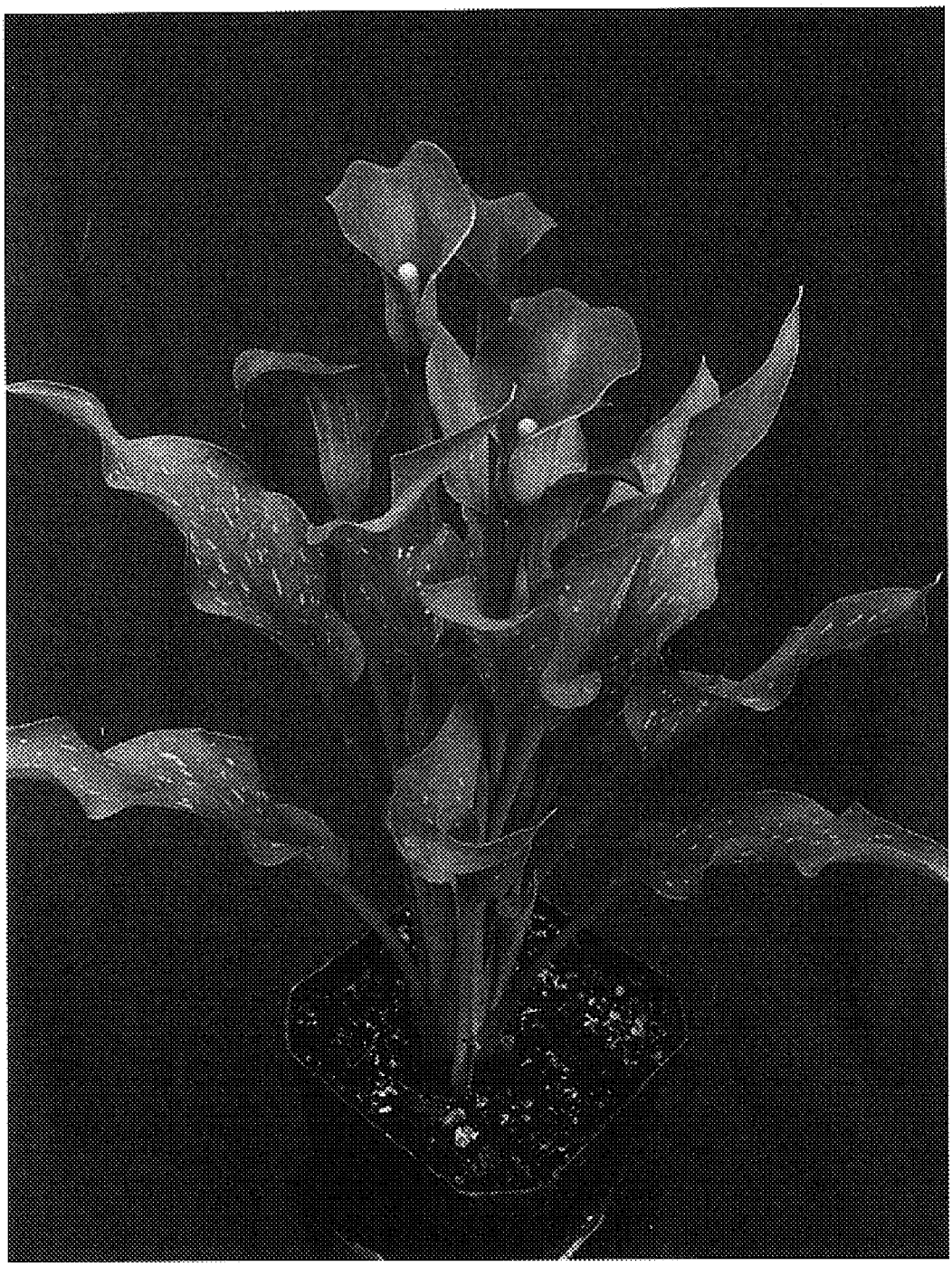
FIG. 2 shows the overall plant habit.
Figure 3:
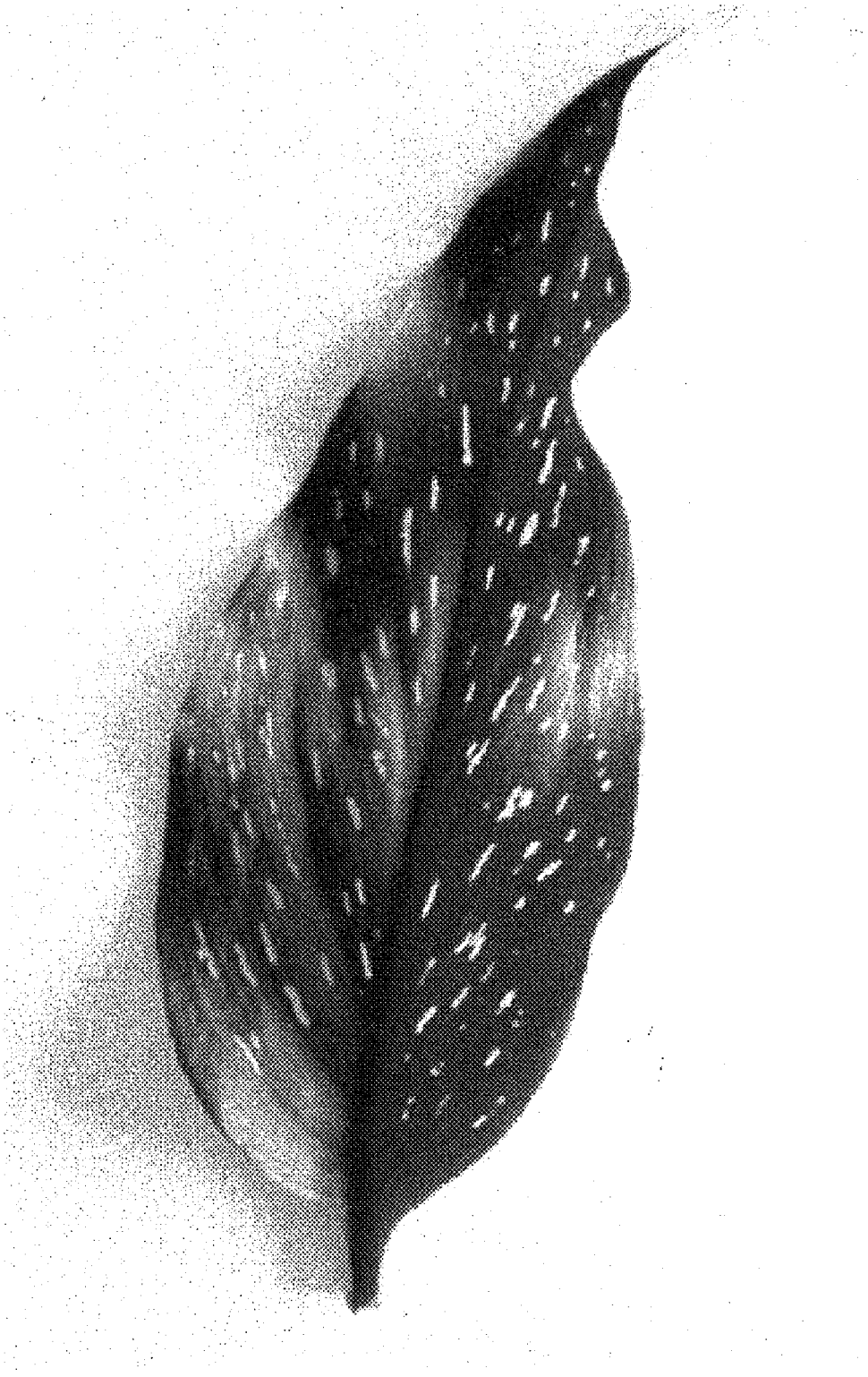
FIG. 3 shows a close-up of the leaf.

The following detailed descriptions set forth the distinctive characteristics of 'Crackerjack'. The data that defines these characteristics were collected from asexual reproductions carried out in New Zealand. The plant history was taken on 2 year old plants based on a 3 cm diameter tuber under New Zealand Summer conditions. Color references are primarily to The R.H.S. Colour Chart of The Royal Horticultural Society of London (R.H.S.).

THE PLANT

Classification:
- *Botanical.*—*Zantedeschia* sp.
- *Commercial.*—*Calla* lily.
- *Variety.*—'Crackerjack'.

Size:
- *Form.*—Erect.
- *Height of the leaf canopy above the soil.*—25–40 cm.
- *Height of top of inflorescence above the soil.*—30–40 cm.
- *Diameter.*—20–30 cm.
- *Number of inflorescence per tuber size.*—Tuber diameter 3 cm.: 2–3. Tuber diameter 4 cm.: 3–5. Tuber diameter 5 cm.: 4–7.

Branches:
- *Character.*—Strong.
- *Color.*—Upper surface is green RHS 146C; lower surface is green RHS 146D; base is white RHS 155B.
- *Average number.*—3–5.

Leaves:
- *Size.*—Width 6–8 cm; length 14–20 cm.
- *Shape.*—Ovate.
- *Color.*—Upper surface is green RHS 137B; lower surface is green RHS 137C.
- *Maculation* (*leaf spots*).—Medium density; white RHS 155C.
- *Apex.*—Acute to apiculate.
- *Margin.*—Moderately wavy, entire.
- *Margin color.*—Yellow-Green RHS 137B.
- *Veins.*—Pinnate.
- *Surface quality.*—Leathery.

Petiole (leaf stalk):
- *Length.*—15–22 cm.
- *Color.*—Green RHS 144A.

Roots:
- *Color.*—White.
- *Branching.*—Not branched, attached to the top of the tuber at the apices.
- *Disease resistance.*—No susceptibility noted to date.
- *Pest resistance.*—No susceptibility noted to date.

THE INFLORESCENCE

Spathe (flower body):
- *Size.*—Length 6–8 cm; width 4–5 cm.

*Color.*—Upper surface is Dark red RHS 59A, base is RHS 154A changing to more yellow toward middle of spathe; lower surface is red RHS 46B.

*Veins.*—Present, red RHS 47A.

*Shape.*—Cupped, acute apex, entire way margin.

Spadix (reproductive organs):

*Size.*—Length 2–3 cm; diameter 0.5–0.7 cm.

*Color.*—Base is green RHS 145A; Middle is dark red RHS 60C; Apex is yellow.

*Position relative to spathe.*—Upright.

Peduncle (flower stem):

*Size.*—30–40 cm.

*Color.*—Base is White RHS 155B; upper is green RHS 146B.

Reproductive organs:

*Location of female organs.*—Basal position of the spadix.

*Location of male organs.*—Upper position of the spadix Perianth (the floral envelope — calyx and corolla) Conspicuous.

*Stamens.*—Not visible before pollen release.

*Pistil.*—16–20 per spadix; green.

Miscellaneous:

*Time to produce a finished flowering plant.*—6–8 weeks.

*Lastingness of bloom on the plant.*—1–3 weeks.

*Fragrance.*—None.

Fruit:

*Production.*—16–20 berries.

*Color.*—Predominantly dark red RHS 60A.

COMPARISON WITH KNOWN CULTIVARS

When the instant plant is compared to 'Pink Pot' (U.S. Plant Pat. No. 14,531) 'Crackerjack' has a courser maculation on the leaves and a flower color that is more "brick" red instead of bright pink. Additionally, the color of the leaves is darker green and has a slight gloss over the leaves.

When the instant plant is compared to the female parent, 'Sunglow', 'Crackerjack' has bright red spathes and ovate glossy green foliage whereas 'Sunglow' has yellow-orange spathes. 'Crackerjack' is distinguished from the male parent primarily in spathe color.

I claim:

1. A new and distinct cultivar of *calla* lily plant as shown and described herein.

* * * * *